US012070392B2

(12) United States Patent
Ng

(10) Patent No.: US 12,070,392 B2
(45) Date of Patent: Aug. 27, 2024

(54) PROSTHETIC STEM FOR A PROSTHETIC IMPLANT

(71) Applicant: University of Maryland, Baltimore, Baltimore, MD (US)

(72) Inventor: Vincent Y. Ng, Reisterstown, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 17/739,715

(22) Filed: May 9, 2022

(65) Prior Publication Data
US 2022/0354656 A1 Nov. 10, 2022

Related U.S. Application Data

(60) Provisional application No. 63/185,470, filed on May 7, 2021.

(51) Int. Cl.
*A61F 2/36* (2006.01)
*A61F 2/30* (2006.01)
*A61F 2/46* (2006.01)

(52) U.S. Cl.
CPC ........ *A61F 2/3676* (2013.01); *A61F 2/30767* (2013.01); *A61F 2002/30548* (2013.01);
(Continued)

(58) Field of Classification Search
CPC .......... A61F 2002/30548; A61F 2/3672; A61F 2/3676; A61F 2/3662; A61F 2002/4631
See application file for complete search history.

(56) References Cited

U.S. PATENT DOCUMENTS

| 4,562,598 A | 1/1986 | Kranz | |
|---|---|---|---|
| 4,892,550 A * | 1/1990 | Huebsch | A61B 17/8822 623/23.19 |

(Continued)

FOREIGN PATENT DOCUMENTS

| CA | 2111598 | 6/1994 |
|---|---|---|
| CN | 203873918 U | 10/2014 |
| EP | 0074981 | 9/1985 |

*Primary Examiner* — Javier G Blanco
(74) *Attorney, Agent, or Firm* — Whiteford, Taylor & Preston, LLP; Gregory M. Stone

(57) ABSTRACT

A prosthetic stem is configured to reduce the perioperative and intraoperative risk of catastrophic medical complications and death that may be caused by BCIS. The prosthetic stem includes one or more internal channels that are configured to self-regulate intramedullary pressure within a prepared bone channel as the stem is inserted into the channel, thus reducing the likelihood of BCIS without sacrificing biomechanics and maintaining a reliable and repeatable implantation process. The stem includes a head and a body, wherein the head is configured to serve as a joint replacement and the body is configured for insertion into the prepared bone channel of a patient. One or more internal channels in the stem are configured to control the pressure within the prepared bone channel during insertion of the stem into the channel, particularly by forming a path through which excess cement may flow as the stem proceeds into the prepared bone channel. By so limiting pressurization of cement during this process, the risk of BCIS complications and other potential harmful effects are reduced while still maintaining sufficient fixation of the prosthetic stem in the prepared bone channel.

9 Claims, 3 Drawing Sheets

(52) U.S. Cl.
CPC ............... *A61F 2002/4631* (2013.01); *A61F 2220/0033* (2013.01); *A61F 2310/00011* (2013.01)

(56) References Cited

U.S. PATENT DOCUMENTS

| | | | |
|---|---|---|---|
| 5,376,123 A * | 12/1994 | Klaue | A61B 17/8802 623/23.19 |
| 6,136,035 A | 10/2000 | Lob et al. | |
| 6,926,741 B2 | 8/2005 | Kolb | |
| 10,433,965 B2 * | 10/2019 | de Beaubien | A61F 2/3609 |
| 2004/0006392 A1 | 1/2004 | Grusin et al. | |
| 2010/0217401 A1 * | 8/2010 | de Beaubien | A61F 2/4241 623/20.36 |
| 2016/0310281 A1 * | 10/2016 | Yeh | A61F 2/3662 |

* cited by examiner

PROSTHETIC STEM FOR A PROSTHETIC IMPLANT

CROSS-REFERENCE TO RELATED APPLICATIONS

This application claims the benefit of U.S. Provisional Patent Application No. 63/185,470 titled "Prosthetic Implant with a Dynamic Seal," filed by the inventor herein on May 7, 2021, the specification of which is incorporated herein by reference in its entirety.

FIELD OF THE INVENTION

The present invention relates generally to prosthetic implants, and more particularly to systems and methods of providing a prosthetic implant in a manner that reduces and manages the pressure inside of a prepared bone channel during implantation into the prepared bone channel to reduce the perioperative and intraoperative risk of catastrophic medical complications and death.

BACKGROUND

Over one million joint replacements are performed in the U.S. per year, and the number is projected to increase significantly over the next several decades. The global market for joint replacements is estimated to be over $23 billion by 2027. Use of a particular cement known as polymethylmethacrylate (PMMA) is a reliable method of securing the stem of orthopedic prostheses within bone and, in some situations, is the most used mode of fixation. Unfortunately, one drawback of using bone cement is the risk of Bone Cement Implant Syndrome (BCIS).

BCIS is a well-described phenomenon and is present in 28% of patients undergoing cemented hemiarthroplasty and 75% in patients with cancer. Mortality within 48 hours is as high as 28% of patients who experience grade 2 or 3 BCIS. The intraoperative mortality rate for elderly patients with hip fractures is 0.2-1.6% and for cancer-related fractures is 4.3%. When the intramedullary canal is filled with liquid cement and a stem is inserted into the canal, there is a significant increase in intramedullary pressure, as previously existing cemented stems are solid and therefore act like a "plunger" within the intramedullary canal, creating high pressures which can lead to BCIS. More particularly, the insertion of the stem of the prosthetic into the prepared bone channel that has received cement for permanent attachment of the prosthetic may cause embolization of fat, air, cement particles, and aggregates of platelets, fibrin and bone marrow into the patient's venous system and subsequently right ventricular dysfunction, increased pulmonary circulation pressures, and cardiovascular collapse. Although there are surgical and anesthetic measures that can be followed in order to attenuate that risk, none are completely effective and BCIS remains a significant cause of intraoperative risk, morbidity, and occasionally, mortality.

Cemented implants are used mostly in elderly patients and cancer patients, two of the highest risk groups for BCIS. Each year, 300 thousand elderly Americans are hospitalized for hip fractures and close to 300 thousand more Americans have metastatic bone disease of which up to 30% will have at least one pathologic fracture. One-third of all patients older than 80 will suffer a hip fracture. If the perioperative risk of death attributable to cementation is conservatively estimated at 1%, the age-adjusted incidence of femoral neck fractures is 63.3 and 27.7/100,000 person-years for women and men, respectively, and University of Maryland Medical System treats one-fifth of all Marylanders (total population 6 million), it calculates out to about 550 femoral neck fractures and potentially 5 lives saved per year in this institution alone.

Thus, there remains a clear need in the art for cemented implants, and methods of their implantation, that reduce the risk of death and other ill effects from BCIS resulting from the implantation of such devices.

SUMMARY OF THE INVENTION

Disclosed herein is an improved prosthetic stem configured to reduce the perioperative and intraoperative risk of catastrophic medical complications and death that may be caused by BCIS, in comparison to typical prosthetic stems. In accordance with certain aspects of an embodiment of the invention, the prosthetic stem includes one or more internal channels that are configured to self-regulate intramedullary pressure within a prepared bone channel as the stem is inserted into the channel, thus reducing the likelihood of BCIS without sacrificing biomechanics and maintaining a reliable and repeatable implantation process. In an exemplary configuration in accordance with aspects of the invention, the stem includes a head and a body, wherein the head is configured to serve as a joint replacement and the body is configured for insertion into the prepared bone channel of a patient. One or more internal channels in the stem are configured to control the pressure within the prepared bone channel during insertion of the stem into the channel, particularly by forming a path through which excess cement may flow as the stem proceeds into the prepared bone channel. By so limiting pressurization of cement during this process, the risk of BCIS complications and other potential harmful effects are reduced while still maintaining sufficient fixation of the prosthetic stem in the prepared bone channel, such as in elderly and cancer-afflicted patients who are most at risk for BCIS and catastrophic complications.

In accordance with certain aspects of an embodiment of the invention, a prosthetic stem for a prosthetic implant is provided, comprising: a shaft body having a shaft body distal end and a shaft body proximal end, wherein the shaft body proximal end is affixed to a prosthetic implant; and a body channel extending from an inlet opening in the shaft body distal end through the shaft body toward and in fluid communication with at least one outlet opening in the shaft body proximal end.

In accordance with further aspects of an embodiment of the invention, a method for implanting a prosthetic implant is provided, comprising the steps of: providing a prosthetic implant having a prosthetic stem, the prosthetic stem further comprising: a shaft body having a shaft body distal end and a shaft body proximal end, wherein the shaft body proximal end is affixed to a prosthetic implant; and a body channel extending from an inlet opening in the shaft body distal end through the shaft body toward and in fluid communication with at least one outlet opening in the shaft body proximal end; preparing a bone channel in a bone of a patient to form a prepared bone channel having cement therein; and inserting the shaft body into the prepared bone channel to cause cement to flow through the inlet opening into the body channel and toward the outlet opening.

Still other aspects, features and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized. The present invention is illustrated by way of example, and not by way of limitation, in the figures of the accompanying drawings, in which like reference numerals refer to similar elements, and in which:

DETAILED DESCRIPTION OF THE PREFERRED EMBODIMENTS

Figure 1:
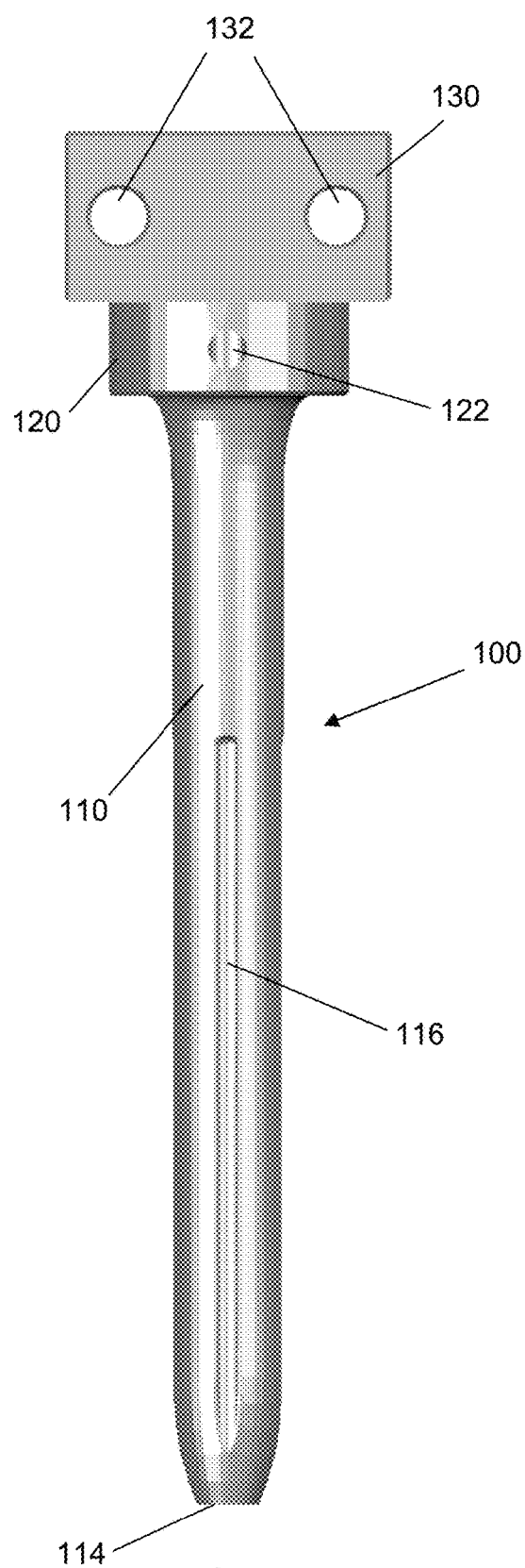
FIG. 1 is a front view of a prosthetic stem in accordance with certain aspects of an embodiment of the invention.
Figure 2:
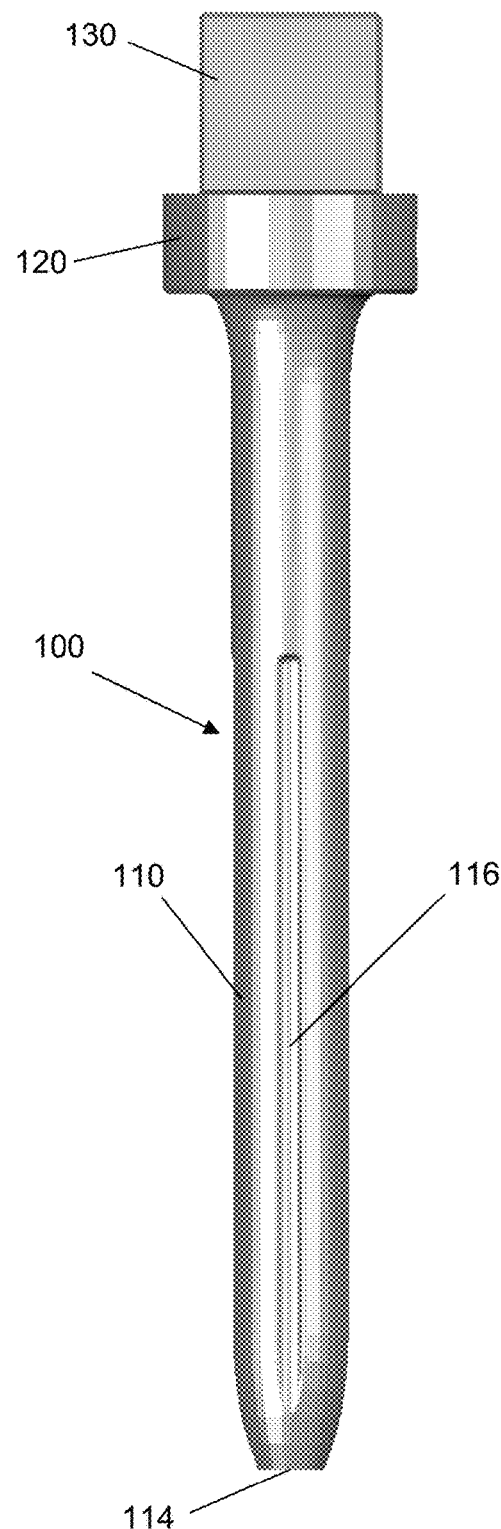
FIG. 2 is a side view of the prosthetic stem of FIG. 1.
Figure 3:
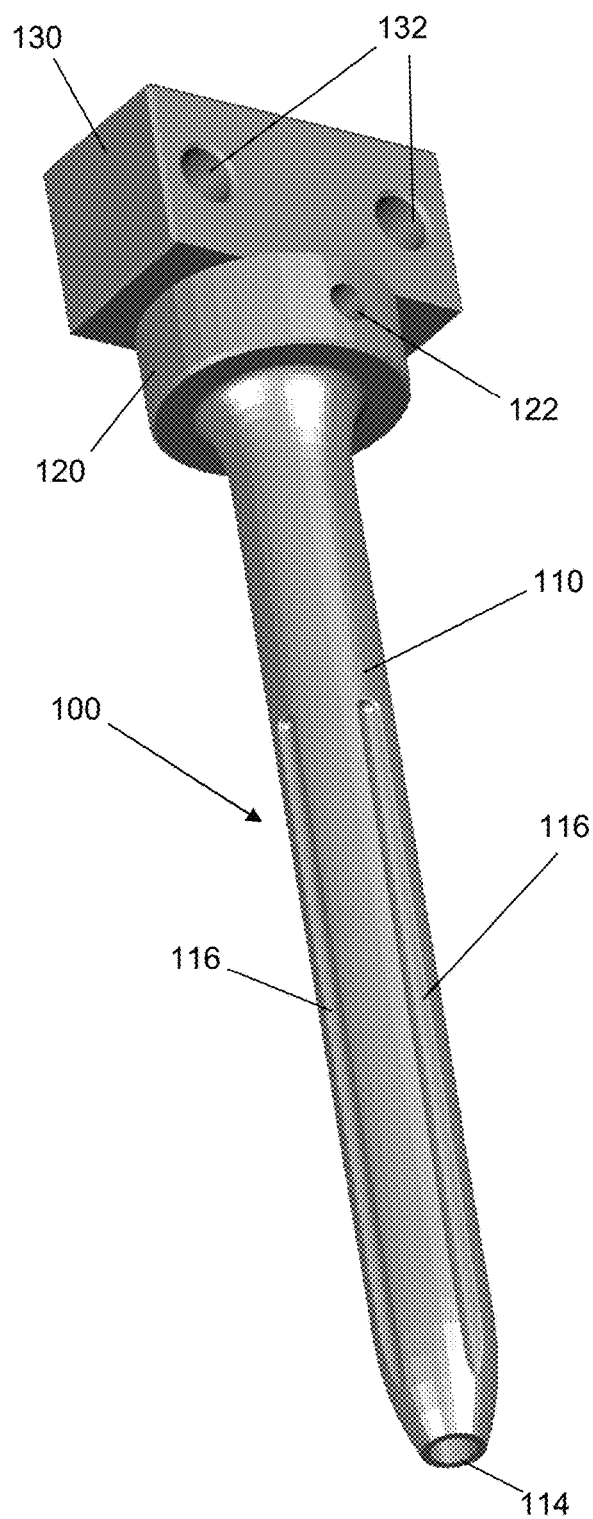
FIG. 3 is a perspective view of the prosthetic stem of FIG. 1.
Figure 4:
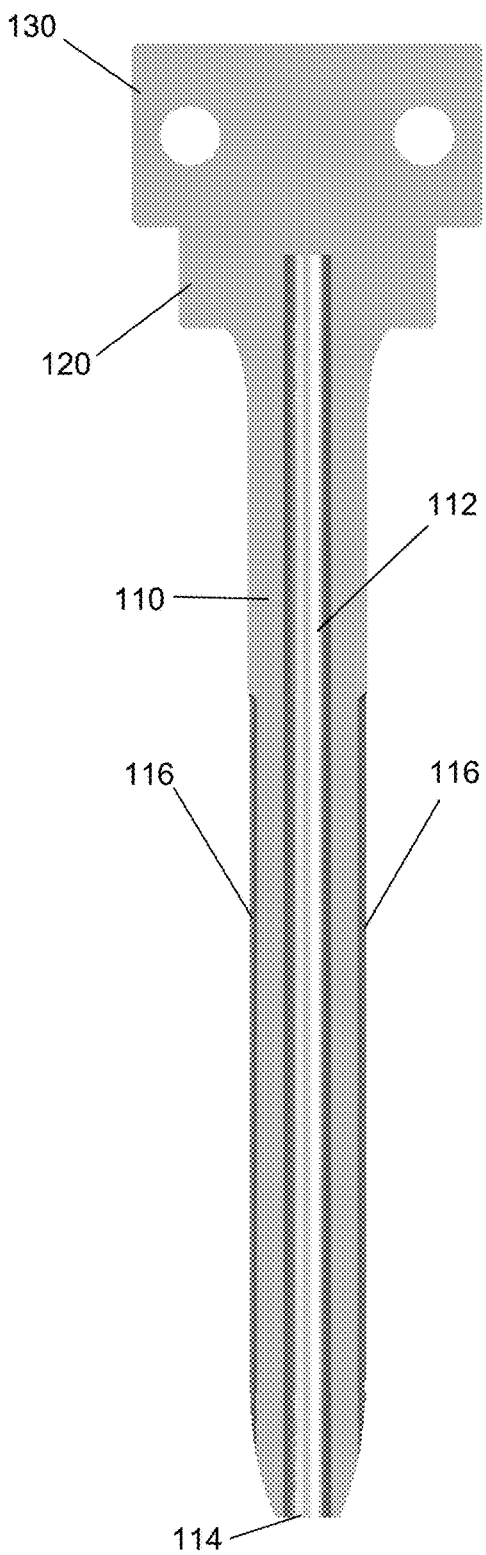
FIG. 4 is a cross-sectional view of the prosthetic stem of FIG. 1.

The following detailed description is provided to gain a comprehensive understanding of the methods, apparatuses and/or systems described herein. Various changes, modifications, and equivalents of the systems, apparatuses and/or methods described herein will suggest themselves to those of ordinary skill in the art.

Descriptions of well-known functions and structures are omitted to enhance clarity and conciseness. The terminology used herein is for the purpose of describing particular embodiments only and is not intended to be limiting of the present disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced items.

The use of the terms "first", "second", and the like does not imply any particular order, but they are included to identify individual elements. Moreover, the use of the terms first, second, etc. does not denote any order of importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Although some features may be described with respect to individual exemplary embodiments, aspects need not be limited thereto such that features from one or more exemplary embodiments may be combinable with other features from one or more exemplary embodiments.

As shown in FIGS. 1-4, and in accordance with certain aspects of an embodiment of the invention, a stem 100 is provided that is particularly configured to allow a physician to control a pressure of cement against an inner surface of a prepared bone channel caused by reduced volume when the stem is inserted into the prepared bone channel. As shown in FIGS. 1-4, stem 100 includes a body 110 that extends distally from a head 130. A stem collar 120 may be provided between body 110 and head 130. Body 110 includes a channel 112 that extends from the distal tip of body 110 upwards toward head 130 and ultimately to an outlet opening 122 in collar 120 or head 130 that is in fluid communication with channel 112, such that cement (or other fluids) flowing into channel 112 at the distal end 114 of body 110 may flow through channel 112 to and out from outlet opening 122, all as further discussed below. In configurations of stem 100 that include collar 120, an undersurface of collar 120 (facing stem body 110 and thus the cut surface of the patient's bone) may be smooth or may have a roughened texture or coated surface, as may be desirable for various patient pathologies. Likewise in such configurations of stem 100 that include collar 120, cylindrical body 110 of stem 100 may flare outwards as it approaches collar 120 and thus increase in diameter near and adjacent to collar 120.

While head 130 is shown in the figures as a rectangular block for simplicity of the instant description, those of ordinary skill in the art will readily recognize that head 130 in fact would be configured as a prosthetic joint for a prosthetic stem, or as a portion of stem 100 that is particularly configured for attachment to such a prosthetic joint. For example, head 130 may be configured as a knee joint, a hip joint, or the like, or in any shape convenient for attachment to a prosthetic knee joint, hip joint, or the like, all as discussed in further detail below. In this regard, head 130 may include one or more openings 132 that may receive screws or similarly configured fixation devices for attaching stem 100 to a prosthetic joint. Of note however, is that a head 130 in any configuration formed as a part of a stem 100 configured in accordance with at least certain aspects of the invention will enable the control of pressure within the prepared bone channel of a patient's bone during insertion of the stem 100. Thus in each such configuration, fluid may flow from within the prepared bone channel, into distal end 114 of body 110, through channel 112, and ultimately to outlet opening 122 when forced by increased pressure within the prepared bone channel that results as the stem 100 is inserted into that bone channel. Such outlet opening may be open to the operating environment or alternatively attached to a conduit, such as a suction conduit, in each case enabling the limitation of pressurization within the prepared bone channel in order to increase safety while providing sufficient fixation of the prosthetic stem 100, such as in elderly and cancer-afflicted patients who are most at risk for BCIS and catastrophic complications.

With continuing reference to FIGS. 1-4, body 110 of stem 100 is configured to fix within a prepared bone channel. As noted above, body 110 of stem 100 is coupled to head 130 at a proximal end of body 110, either directly or through a collar 120. Opposite the proximal end of body 110, the body defines a distal tip at the distal end 114 that is inserted into the patient's prepared bone channel (e.g., a prepared bone channel having cement). Body 110 of stem 100 preferably has a generally cylindrical shape. In certain configurations, body 110 of stem 100 includes a taper as its length approaches distal end 114 in order to ease insertion of stem 100 into a prepared bone channel. For example, distal end 114 of body 110 may be pointed to define a pointed distal tip. Likewise in certain configurations, body 110 can have an elliptical cross-section, or a cross-section that varies between the distal end 114 and a proximal end of stem 100. Still further, stem 100 may be straight or alternatively may be bowed, such as to match the curvature of a patient's femur. Still further, body 110 of stem 100 may be shaped to match the general contour of the metaphyseal portion of the patient's bone as in a traditional hip arthroplasty femoral stem.

Furthermore, central channel 112 of body 110 of stem 100 is configured to fluidly couple a volume surrounding the distal tip to the proximal end of channel 112 that communicates with outlet opening 122. In certain configurations, central channel 112 extends between the open aperture of the distal tip and the proximal end at outlet opening 122. Likewise in certain configurations, central channel 112 is generally centrally positioned within body 110 and extends along a central axis of stem body 110 between the distal end 114 and its proximal end. Channel 112 may extend generally parallel to the central axis of stem 100. The aperture near the distal end 114 of stem body 110 may in certain configurations be located on or towards a side of the distal end (e.g., not aligned with a central axis of the body). Likewise in certain configurations, the distal end 114 of body 110 may include a plurality of apertures fluidly coupling the prepared bone channel to the central channel 112. Likewise, body 110 of stem 100 may include apertures (similar to an aperture near distal end 114) along a length of body 110 between the distal end 114 and the proximal end of stem 100 to fluidly couple the prepared bone channel to the central channel. Thus, stem 100 may allow fluid flow to limit pressurization in a prepared bone channel to increase safety while providing sufficient fixation of the prosthetic stem.

With continuing reference to FIGS. 1-4, stem 100 can be formed according to typical manufacturing methods. For example, stem 100 can be formed of metals, ceramics, plastics or the like, and may be formed by casting, forging, machining, additive manufacturing, or the like. For example, in certain configurations stem 100 may be formed of a cobalt chrome, stainless steel, titanium, and/or combinations of the foregoing. Likewise in certain configurations, stem 100 may be formed by casting. Still further, stem 100 can include surface treatments configured to increase the likelihood of fixation within a prepared bone channel. For example, an outer surface of body 110 of stem 100 may include a roughened, knurled, or porous surface that effectively increases the surface area for fixation (e.g., with cement to the prepared bone channel).

In certain exemplary configurations, the fluid opening at the distal end 114 of body 110 of shaft 100 may removably receive a solid tip (such as via threads or other similarly configured connection mechanisms) in order to increase the versatility of stem 100 and enable its use as a traditional solid stem where and when desirable.

The particular dimensions and shape of the channel or channels inside of the stem 100 from the inlet at distal end 114 to the outlet opening 122, as well as the outlet opening (or openings) 122 itself, may be particularly configured to enable a desired pressure profile to be maintained as the stem is inserted into the prepared bone channel.

For example, in certain configurations at least one egress channel is provided between and in fluid communication with both channel 112 and outlet opening 122, which egress channel can be configured for specific procedures and circumstances. By way of non-limiting example, stem collar 120 or head 130 may include a plurality of egress channels extending from the proximal end of channel 112 to outlet opening (or multiple outlet openings) 122 to increase a flow rate of liquid through channel 112 from the patient's prepared bone opening to outlet opening 122. Likewise, each of a plurality of egress channels may have varying diameters and curvilinear pathways between channel 112 and the environment outside of channel 112 through outlet opening 122. Furthermore, such egress channels can have an aperture 122 to the environment at various positions on the stem collar 120 or head 130, depending on the procedure and application (e.g., patient diagnosis, joint, bone and joint damage, etc.). In certain exemplary configurations, at least one outlet opening 122 is positioned along a generally central axis of the stem collar 120 or head 130. Likewise in certain exemplary configurations, at least one outlet opening 122 aperture is generally parallel to a central axis of the stem body 110 (i.e. parallel to a major axis of the body, as described below).

Likewise in certain configurations, multiple outlet openings 122 may be provided, which may facilitate easier cleaning of cement by a surgeon, depending upon soft tissue anatomy and access to the outlet openings 122 intraoperatively (i.e., if soft tissues are blocking visualization of a posterior outlet opening 122, the surgeon may block that posterior outlet opening in order to have cement exit only through an anterior outlet opening 122, etc.). In any case, the total area for fluid outlets from channel 112 would typically approximate the area or volume flow rate for the inlet of channel 112 in order to prevent creation of a log jam with the egress of cement. Likewise in any case, the total opening area of multiple outlets 122 would typically be the same as the total opening area of a configuration of stem 100 having a single outlet 122.

Outlet opening or openings 122 may be positioned on stem 100 such that one or more openings 122 open into the patient's intramedullary canal when stem 100 is fully inserted into the prepared bone channel (i.e., may transfer cement or pressure within the intramedullary canal). By placing one or more openings 122 in this manner so that it opens to the patient's intramedullary canal, pressure may be decompressed during the initial insertion of the stem, but thereafter once the stem 100 is nearly fully inserted (i.e., the outlet opening 122 is sunk past the introitus of the patient's bone), the intramedullary canal will not further decompress (because the outlet opening 122 is within the bony canal) and pressure at that point is maintained.

Still further, the shape and size of channel 112 and opening or openings 122 may be of constant diameter or of varying diameters, although in each configuration channel 112 should be at least as large as the inlet opening at distal end 114 of body 110. For example, channel 112 may be provided an internal diameter that is larger than a diameter of the inlet at distal end 114 of body 110, which may facilitate greater decompression of the cement than if those diameters were equal, such as by providing less resistance once the cement enters the inlet opening. Likewise, providing the inlet opening at distal end 114 with a slightly smaller diameter than channel 112 may ensure that some cement remains inside the prepared bone channel to form a cement mantle, and so that all of the cement does not simply enter into and travel upward through channel 112. Still further, providing an outlet opening 122 having a diameter that is smaller than the inlet opening at distal end 114 of body 110 may allow maintenance of at least some pressure towards the end of the insertion process, because air will still be capable of escaping while the cement enters the channel 112, such that it should not impede flow of cement until the cement ultimately reaches the outlet opening 122. This configuration may also limit the amount of extruded cement that results from the insertion process, thus limiting the amount of extruded cement that the surgeon must clean up and remove during the surgical procedure.

In exemplary configurations, channel 112 has a diameter of at least 5 mm in order to allow an adequate flow rate of a viscous fluid (such as typical cements used in the cemented implantation of prostheses) through the channel to effectively reduce pressure as intended while still ensuring proper fixation of stem 100 in the patient's prepared bone channel.

Likewise, channel 112 may itself exhibit a tapering and/or enlarging diameter from the inlet at distal end 114 of body 110 to outlet opening 122. The diameter and general cross-sectional shape of channel 112 may vary along its length to affect a desired change in pressure during the insertion process (e.g., increase or decrease pressure as stem 100 is inserted by varying the cross-section of channel 112).

In light of the above, those skilled in the art will recognize that the inlet opening of channel 112 at distal end 114 of body 110, the outlet opening 122, and channel 112 may be of the same or of differing sizes. For instance, the inlet opening at distal end 114, channel 112, and outlet opening 122 may have a size ratio that is 1:1:1 (inlet, channel, outlet), but ranges between 1:1-3:0.25-2 may likewise be suitable and selected in order to achieve a particularly desirable pressure profile. Likewise, as individual patient anatomical sizes obviously differ, stems 100 may be provided having varying diameters or lengths of body 110, which in turn may vary the diameter or length of channel 112. Even further, the shape and/or contour of channel 112 may be configured to meet varying objectives. For example, channel 112 may be defined by a smooth, cylindrical surface, or it may have grooves of other varying contours. Likewise, the exterior of body 110 of stem 100 may be smooth or may be provided longitudinal grooves 116. Grooves 116 may in certain configurations align with grooves on the interior channel 112 to strengthen the walls of stem 100. Exterior of body 110 may further have a matte or highly polished or roughened exterior surface along stem 100, and may be provided varying textures or coatings, such as highly polished, matte, knurled, roughened or porous with hydroxyapatite coating provided proximally to facilitate bone ingrowth. Still further, inner channel 112 may be in the shape of a fusiform, such that the inner channel 112 can be larger than the inlet opening at distal end 114 or the outlet opening 122, but maintaining a smooth transition between such varying diameter regions.

Figure 5:
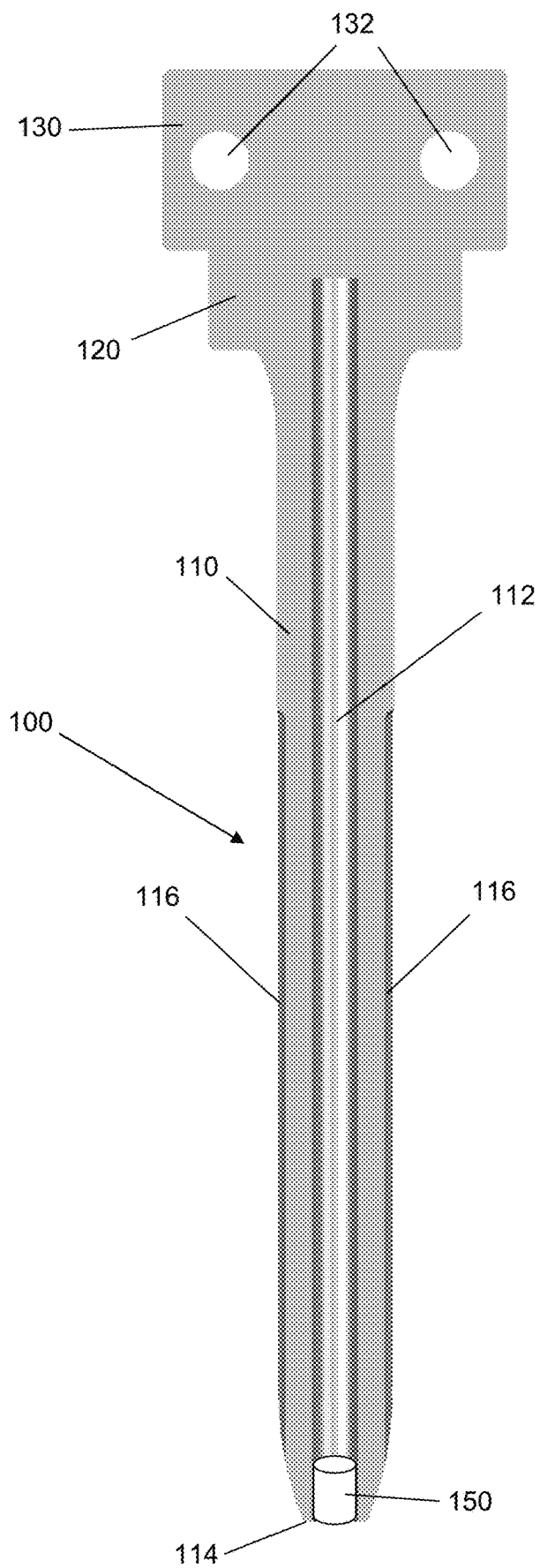
FIG. 5 is a cross-sectional view of the prosthetic stem of FIG. 1 and including a dynamic seal.

In addition to the dimensions and shape of the channel or channels inside of the stem, a dynamic seal in the form of, for example, a valve or a pressure-responsive plug or the like may also be provided to further control the pressure realized in the prepared bone channel as the stem is inserted into the bone channel. By way of non-limiting example and with particular reference to FIG. 5, stem 100 may be provided a dynamic seal 150 configured to regulate pressure within central channel 112 and the patient's prepared bone channel. In certain configurations, the dynamic seal 150 comprises a slidable plug that is configured to limit pressurization in a prepared bone channel and central channel 112. For example, dynamic seal 150 can be a bullet-shaped component having a tapered end 152 configured to translate within channel 112 of the stem 100 between the distal end 114 and the proximal end of stem 100. Likewise in certain configurations, dynamic seal 150 may be initially positioned at the distal tip 114 at least partially inside of central channel 112, i.e. at the aperture of the opening at distal end 114 of body 110.

Inserting stem 100 into the patient's prepared bone channel having a fluid or fluid-like substance, e.g., cement, increases fluid pressure (e.g., static pressure of the fluid or cement) on dynamic seal 150. The fluid pressure slidably translates dynamic seal 150 proximally toward head 130 of stem 100. The dynamic seal 150 slidably translates within central channel 112, which increases the volume in which fluid or cement within the prepared bone channel can flow (i.e., is available to flow). Affecting the available volume further affects the pressure of the fluid or cement inside of the patient's prepared bone channel, and for example may be inversely proportional to the volume. Thus, increasing the available flow volume by sliding dynamic seal 150 from (or near to) distal tip 114 towards the proximal end of the central channel 112 reduces the pressure of the fluid or cement in the prepared bone channel, for example, as the prosthetic stem is inserted into the prepared bone channel.

As described above, dynamic seal 150 may be configured to slidably translate from near distal tip 114 toward the proximal end of central channel 112. Dynamic seal 150 may be further configured to slidably translate through a portion of channel at the proximal end of channel 112, i.e., near or in stem collar 120 and/or head 130. Such proximal portion of channel 112 may be further configured to stop the dynamic seal's translation, for example, by having a cross-section in a portion of channel 112 that frictionally stops dynamic seal 150 from further translating within channel 112. In certain configurations, dynamic seal 150 has a shape and size (e.g., a cross-sectional shape and size) relative to central channel 112 configured to create a predetermined amount of frictional force with central channel 112. For example, dynamic seal 150 may have a cylindrical-like shape with a diameter slightly less than the diameter of the major portion of channel 112 but that closely matches a more narrow diameter of channel 112 at its proximal end, in order to increase the friction (i.e., while slidably translating) as the dynamic seal 150 approaches the proximal end of channel 112, thereby achieving an approximate predetermined rate of translation for a rate of stem insertion into the patient's prepared bone channel. Thus, the rate of translation can be adjusted according to several parameters, including the size and shape of central channel 112, the size and shape (including cross-section and length) of dynamic seal 150, and the material of dynamic seal 150. In certain configurations, dynamic seal 150 can be formed of a plastic, rubber, or metal. Thus, the proximal end of channel 112 and dynamic seal 150 may be configured to stop the translation of dynamic seal 150 and limit the increase of available volume.

Likewise with this configuration of dynamic seal 150, ultimate egress of cement to and through outlet opening 122 may be blocked and thus not flow out from channel 112, in turn stopping the reduction of intramedullary pressure at a desired level. Thus, stem 100 may be configured to limit and in fact control pressurization of cement in order to increase safety while providing sufficient fixation of the prosthetic stem, compared to typical stems, such as in elderly and cancer-afflicted patients who are most at risk for BCIS and catastrophic complications.

Dynamic seal 150 may thus prevent cement ingress into channel 112 until a certain desired intramedullary pressure is reached. Dynamic seal 150 may be formed of polyethylene, and thus may be way of non-limiting example comprise a polyethylene stopper configured to be ejected at a predesignated pressure. Dynamic seal 150 may likewise comprise a polyethylene flap or shutter configured such that a pre-designated pressure will open the flap or shutter to allow cement to pass into channel 112, thus enabling the control of pressure at the inlet opening at distal end 114 of body 110 and/or at the outlet opening 122 and/or within channel 112.

Still further, pressure within the prepared bone channel may be further controlled by monitoring pressure at outlet opening 122, such as through use of a manometer or other pressure-measuring device, and taking measures to increase or decrease pressure in channel 112 (and in the prepared bone channel) as appropriate and as discussed elsewhere herein. For example, a traditional solid-type prosthetic stem can create maximal insertion pressures of 110 PSI (758 kPa). Prosthetic stems formed in accordance with at least certain aspects of an embodiment of the invention may have a maximal insertion pressure of 60 PSI (413 kPa) with a solid stem, of 40 PSI (275 kPa) with a channel 112 and a dynamic seal 150, and of 20 PSI (138 kPa) with a channel 112 and without a dynamic seal 150 when inserted into a prepared bone channel. According to experiments, minimal acceptable pressures for insertion of 14.5 PSI (100 kPa) are needed to produce adequate cement-bone interdigitation and actual applied pressures can vary from 50-218 PSI (350-1500 kPa). Thus, a prosthetic stem 100 configured in accordance with at least certain aspects of the invention may be configured to reduce the insertion pressure during cementation to a more desirable range and likely decrease the incidence of BCIS, compared to typical stems.

Stem 100 may form a part of a wide variety of prostheses. More particularly, head 130 may be attached to, or alternatively may itself form (in each case with body 110 of stem 100 extending therefrom as detailed above), a cemented hip arthroplasty stem, a cemented humeral stem, a megaprosthetic cemented stem (i.e., a prosthesis that replaces not only the epiphysis of the bone, but also the metaphysis, and sometimes the diaphysis of the bone), or the like, including for example any cylindrical stem that might be used to implant a megaprosthesis in other parts of the patient's body (e.g., distal femur, proximal femur, proximal tibia, humerus, etc.). Stem 100 may thus provide an attractive prosthetic solution for many patients, including elderly patients who have hip fractures or who have varied cancers, as the stem 100 may have an expected lifetime that exceeds the projected survival of the patient and may further reduce the risk of catastrophic complications, such as BCIS.

In use, a surgeon may employ stem 100 in order to control pressure within a prepared bone channel that is to receive prosthetic stem 100. When desired, the surgeon may couple a manometer to the outlet opening 122 to closely monitor pressure inside of channel 112, and thus inside of the prepared bone channel that is in fluid communication with channel 112. After the stem 100 has been fully placed, the manometer and tubing are removed in order to avoid damage from the exothermic reaction that occurs during cement hardening. Further, the surgeon may place one of their fingers or thumb over one or more outlet openings 112 while inserting the stem 100 into the prepared bone channel in order to maintain or increase pressure as desired. Still further, suction tubing may be attached to outlet openings 112 to provide negative pressure and facilitate additional decompression of channel 112 and the bone channel receiving stem 100. Optionally, a collection container or tubing may be provided and attached to outlet opening 112 to reduce spillage of cement into the surgical wound.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. Thus, it should be understood, therefore, that the invention may be practiced otherwise than as specifically set forth herein.

What is claimed is:

1. A prosthetic stem for a prosthetic implant, comprising:
   a shaft body having a shaft body distal end and a shaft body proximal end, wherein said shaft body proximal end is sized and configured to be affixed to a prosthetic implant;
   a body channel longitudinally extending from an inlet opening in the shaft body distal end through said shaft body toward and in fluid communication with at least one outlet opening in said shaft body proximal end;
   an egress channel extending from said body channel to said outlet opening; and
   a pressure-responsive dynamic seal translatable in said body channel sized and configured to prevent passage of fluid through said body channel toward said outlet opening until a predesignated pressure is reached in said body channel upstream from said dynamic seal.

2. The prosthetic stem of claim 1, wherein said egress channel is positioned at an angle to said body channel.

3. The prosthetic stem of claim 1, further comprising a plurality of egress channels extending from said body channel.

4. The prosthetic stem of claim 3, wherein each said egress channel extends from said body channel to a single outlet opening.

5. The prosthetic stem of claim 1, wherein said shaft body is formed of metal.

6. The prosthetic stem of claim 5, wherein said metal is selected from the group consisting of cobalt chrome, stainless steel, titanium, and combinations of the foregoing.

7. The prosthetic stem of claim 1, wherein said body channel has a channel diameter of at least 5 mm.

8. The prosthetic stem of claim 1, wherein said inlet opening is configured to removably receive a solid tip.

9. The prosthetic stem of claim 1, wherein the shaft body has a surface treatment configured to increase the likelihood of fixation within a prepared bone channel.

* * * * *